United States Patent [19]

Kelly

[11] 4,335,095

[45] Jun. 15, 1982

[54] INDIUM-111 OXINE COMPLEX COMPOSITION

[75] Inventor: James D. Kelly, Buckinghamshire, England

[73] Assignee: The Radiochemical Centre Limited, England

[21] Appl. No.: 128,923

[22] Filed: Mar. 10, 1980

[30] Foreign Application Priority Data

Mar. 21, 1979 [GB] United Kingdom ................ 7909867

[51] Int. Cl.$^3$ ...................... A61K 49/00; A61K 43/00
[52] U.S. Cl. ........................................... 424/1; 424/9
[58] Field of Search ....................................... 424/1, 9

[56] References Cited

U.S. PATENT DOCUMENTS 3,728,351  4/1973  Counsell et al. ........................ 424/1
4,017,596  4/1977  Loberg et al. .......................... 424/1

FOREIGN PATENT DOCUMENTS 2390408  1/1979  France ................................. 424/1.5

OTHER PUBLICATIONS

Merrick et al., from Medical Radioisotope Scintigraphy 1972, IAEA, Vienna, 1973, pp. 721-729.
Heindel et al., Ed., The Chemistry of Radio Pharmaceuticals, Masson Publishing USA, Inc, New York (1978), p. 43.
Thakur et al., Chemical Abstracts, vol. 87, 1977, Abstract #35098m.

Primary Examiner—Christine M. Nucker
Attorney, Agent, or Firm—Wenderoth, Lind & Ponack

[57] ABSTRACT

An indium-111 preparation comprises a complex of indium-111 with a quinoline compound carrying an 8-hydroxyl group, e.g. oxine, present in an aqueous medium which also contains a surface active agent to prevent the complex from becoming bound to the surface of the vessel on autoclaving, and optionally a buffer to improve blood cell labelling efficiency. The surface active agent is preferably non-ionic, e.g. a polyoxyethylene sorbitan ester of a fatty acid. The buffer is preferably N-2-hydroxyethylpiperazine-N'-2-ethanesulphonic acid.

8 Claims, No Drawings

INDIUM-111 OXINE COMPLEX COMPOSITION

Indium-111 is a radioactive isotope with a half life of 67 hours. It decays by emitting gamma radiation at energies of 0.173 and 0.247 MeV, convenient for body visualisation and counting with gamma cameras. A complex of indium-111 with oxine (8-hydroxyquinoline) has the formula:

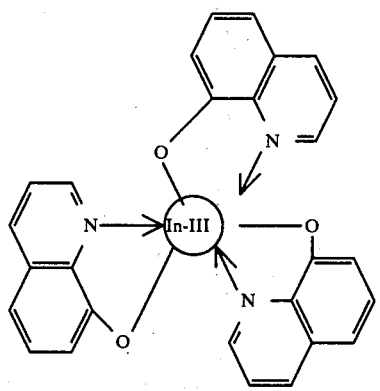

This complex is known and is described, for example, by M. L. Thakur et al in J. Lab. and Clin. Med., Vol. 89(1) Jan. 1977 pages 217 to 228. It is useful for labelling blood cells. Leukocytes labelled with this complex are valuable for detecting abscesses. Labelled platelets can be used to visualise thrombi. The complex is lipophilic, and this property enables it to penetrate blood cells. Once inside the cells, it appears that the complex breaks down and the indium-111 becomes fixed in position.

The complex is easily made, simply by mixing aqueous solutions of a salt of indium-111, generally indium chloride, and 8-hydroxyquinoline. However, presumably owing to its lipophilic properties the complex is not very stable in aqueous solution. It seems that it is capable of remaining in solution in water, but not of being dissolved in water. Moreover, when the aqueous solution is left in contact with a glass or plastics vessel containing the solution, a significant proportion of the complex becomes bound to the glass or other surface of the vessel. This problem of becoming bound to glass surfaces is seriously aggravated by autoclaving the solution.

Because of these difficulties, the standard practice for bringing the complex into a form suitable for labelling blood cells, as described in the above-noted article of M. L. Thakur et al, has involved extraction into chloroform, evaporation of the chloroform to dryness, and then solution in absolute ethyl alcohol. This process is unsatisfactory for several reasons. It takes a long time, and time is of critical importance with a short-lived isotope such as indium-111. There are generally 20% losses of label at the extraction stage. The process involves chemical processing of radioactive materials together with the use of inflammable solvents and dry residues, both of which are difficult and potentially dangerous to handle by remote control. Ethanol solutions of the complex are not self-sterile and cannot be autoclaved; and sterility is of course essential where blood cells are to be labelled for subsequent injection into a patient.

A simpler technique for making the complex in aqueous solution has recently been proposed in French No. 77.14396 (2390408) of Compagnie Francaise Philips, but this does not avoid the problem of the complex becoming bound to the glass or other surface of the vessel.

It is an object of the present invention to overcome these disadvantages. The invention accordingly provides an indium-111 preparation comprising a complex of indium-111 with a quinoline compound carrying a hydroxyl group in the 8-position, present in an aqueous medium which also contains at least 10 µg/ml of a surface active agent.

The preferred complexing agent is 8-hydroxyquinoline (oxine). However, it is envisaged that derivatives of oxine may be used, for example with alkyl, e.g. methyl, or halogen, e.g. chlorine, substituents provided that the ability of the derivative to form a complex having lipophilic properties with indium is retained.

Surface active agents are extensively used in pharmaceutical preparations as emulsifiers and solubilisers. In these circumstances, the surface active agents are rapidly diluted by body fluids immediately after administration to the patient. It is surprising that surface active agents can be used in compositions for labelling blood cells, where only a very limited amount of dilution is possible. It is of course essential that the surface active agent should be non-toxic to the blood cells at the concentration in which it is used. On grounds of low toxicity, we prefer to use non-ionic surface active agents, and specifically a range of polyoxyethylene sorbitan esters of fatty acids, sold under the Trade Mark Tween. At least 10 µg/ml of surface active agent is needed in order to reduce adhesion of the complex to container walls during autoclaving. While there is no critical upper limit on the surface active agent concentration, generally not more than 1,000 µg/ml will be used. In order to avoid damage to the blood cells, the surface active agent concentration of the solution in contact with the blood cells should preferably not exceed 200 µg/ml. The pH of the composition should be such that the complex is stable, and should be tolerated by the blood cells. A pH in the range 5 to 8, preferably around 7, is suitable.

The concentration of the indium-111 is not critical, and may suitably be in the range 0.1 to 10 mCi/ml. The oxine concentration may suitably be in the range 5 to 100, preferably 25 to 50, µg/mCi of indium-111. If the oxine concentration is too low, labelling efficiency is reduced, possibly by competition with other metals. An excessively high oxine concentration involves a possible toxicity hazard, and tends to reduce labelling efficiency.

Another problem that arises with aqueous compositions containing these complexes is that sterilisation by autoclaving quite dramatically reduces blood cell labelling efficiency. While it would in theory be possible to make the complex using sterile ingredients under sterile conditions, it is in commercial practice very much easier and cheaper to sterilise the final product by autoclaving. We have found, and this constitutes a subsidiary aspect of the present invention, that this loss of labelling efficiency on autoclaving can be mitigated by incorporating a buffer in the aqueous composition. Our preferred buffer is N-2-hydroxy-ethylpiperazine-N'-2-ethanesulphonic acid (HEPES). At a concentration of at least 0.01 or 0.02 molar, HEPES is effective to mitigate the loss of labelling efficiency caused by autoclaving. There is no critical upper limit of concentration, although it is preferred to use a concentration not greater than 0.5 M on toxicity grounds. The concentration in the aqueous solution in contact with the blood cells should preferably be not more than 0.02 M, although it is probable that blood cells could tolerate 0.05 M concentration for short periods.

While HEPES is the preferred buffer it is believed that other zwitterionic compounds will also be effective. Indeed any buffer which is non-toxic and compatible with biological systems, and which maintains a pH in the range 5 to 8, for example TRIS buffer or bicarbonate, is suitable.

The compositions of this invention are based on an aqueous medium, although the incorporation of a minor proportion, less than 50%, of a water-miscible organic liquid is possible. Since the compositions are intended, after labelling blood cells, for injection, they are preferably based on isotonic saline solution. The compositions are easily prepared simply by mixing the ingredients, no heating or other treatment being necessary. In the Examples which follow, the compositions contain approximately 1 mCi/ml of indium-111, and 50 μg/mCi of indium-111 of oxine, made isotonic with sodium chloride. Compositions are prepared by the following typical procedure:

To a suitable glass vessel, washed free of metallic ion impurities, the following sterile, pyrogen-free component solutions are added:
1. 0.5 ml of indium-111 chloride at a radioactive concentration of 10 mCi/ml in 0.04 N HCl.
2. 1.0 ml of 8-hydroxyquinoline solution in 0.04 N HCL at a concentration of 250 μg/ml.
3. 1 ml of 1 M HEPES solution, pH 7.2–7.4.
4. 100 μl of 1% Tween-80 in saline.
5. 1.0 ml of pyrogen-free water.
6. 1.4 ml of isotonic saline solution.

The solution is dispensed into vials which are closed and autoclaved at 121° C. for 25 minutes.

Blood cell labelling with this composition is conventional. A sample of the patient's blood is fractionated to separate the desired blood cells, and a suspension of these in a suitable medium is incubated with the indium-oxine complex composition for 1 to 15 minutes. A suitable medium may be saline solution or plasma, depending on what type of cells are being labelled. After incubation, the supernatant is decanted to remove that portion of the indium complex which has not been absorbed by the blood cells, and the cells are re-suspended and re-injected into the patient.

Various compositions were made up according to the above procedure, some in accordance with the present invention and some for comparative purposes, and were subjected to tests:
1. Retention in Vial
  (a) Place a 1 ml sample of indium-111-oxine, at a radioactive concentration of 1 mCi/ml, in a vial. In some cases the vial is autoclaved. Allow to stand for three days.
  (b) Measure the radioactivity of the vial.
  (c) Remove the vial contents through a needle into a syringe.
  (d) Add 1 ml of isotonic saline to the vial.
  (e) Remove the saline.
  (f) Measure the radioactivity of the vial. The retention in the vial is defined as:

$$\frac{\text{(Activity in the empty vial)}}{\text{(Activity in the vial containing the indium-oxine solution)}} \times 100\%$$

2. Blood cell labelling efficiency

Human lymphoblastoid cells (type BeC11), propogated in culture, were obtained commercially at an approximate concentration of $10^7$ cells/ml in a culture medium (RRMI 1640). The following procedure was carried out:
  (a) Put 10 ml of cells in a conical-based vessel, fitted with a screw-cap.
  (b) Spin down the cells in a centrifuge.
  (c) Decant the culture medium.
  (d) Resuspend the cells in 5 ml of isotonic saline.
  (e) Add 0.1 to 0.5 ml of indium-111-oxine solution.
  (f) Incubate for a period of 5 to 15 minutes (the incubation is generally carried out at room temperature, but a range of 4° C. to 37° C. is suitable).
  (g) Spin down the cells.
  (h) Decant the supernatant solution.
  (i) Resuspend the cells in 5 ml of isotonic saline.
  (j) Spin down the cells again, and decant the second supernatant solution (termed the "wash" fraction).
  (k) Resuspend the cells.

The "supernatant," "wash" and "cell" fractions together contain all the activity added at the beginning of the cell labelling operation. The cell labelling efficiency is measured (after counting the indium-111 activity content in the three fractions) as:

$$\frac{\text{(Activity in "cell" fraction)}}{\text{(Activity in "supernatant" + "cell" + "wash" fractions)}} \times 100\%$$

Results are reported in the Tables below.

Table 1 relates to compositions not containing any surface active agent, and shows the effect of increasing HEPES concentration, both before and after autoclaving, on blood cell labelling efficiency.

Table 2 relates to compositions containing 0.2 M HEPES buffer, and shows the effect of two different surface active agents on adhesion to the vial walls both before and after autoclaving.

Table 3 relates to compositions containing 0.2 M HEPES buffer, and shows the effect on vial retention of altering the surface active agent concentration.

Table 4 relates to compositions containing 0.2 M HEPES buffer, and shows the effect on vial retention of various additions to the composition.

Table 5 relates to compositions containing 0.2 M HEPES buffer, and shows the effect of two surface active agents, after autoclaving, on blood cell labelling efficiency.

Table 6 relates to compositions containing 0.2 M HEPES buffer, and shows the effect of different concentrations of surface active agent on blood cell labelling efficiency.

Table 7 compares blood cell labelling efficiency of aqueous compositions of the present invention with prior art ethonolic solutions of indium-111-oxine complex.

Table 8 compares vial retention, for preparations of indium-111-oxine with various buffers, both with and without surface active agent. The radiochemical purity (RCP) of the sample, measured by extraction into n-octanol, is also reported.

TABLE 1
Effect of HEPES Concentration

| (HEPES) | No of days post-prep when labelling efficiency measured | Duplicate determinations of cell labelling efficiency | | | |
|---|---|---|---|---|---|
| | | not autoclaved | | autoclaved | |
| 0.00 | 3 | no data | | 36.7 | 32.9 |
| | 14 | | | 43.9 | 46.6 |
| 0.02M | 1 | 62.0 | 70.0 ⟷ | 45.8 | 44.9 |
| | 15 | 89.4 | 90.0 ⟷ | 65.5 | 64.7 |
| 0.06M | 7 | 92.7 | 91.7 ⟷ | 73.0 | 73.5 |
| 0.20M | 1 | 89.9 | 91.0 ⟷ | 86.5 | 87.2 |

TABLE 2
Retention of Activity in Vials

| | % retained in Vial | |
|---|---|---|
| Surfactant Additive | not autoclaved | autoclaved |
| No additive | 19.3% | 37.5% |
| Tween-80 250 μg/ml | 4.0% | 2.0% |
| Pluronic-F68 2.5 mg/ml | 6.6% | 8.0% |

TABLE 3
Effect of Tween-80 Concentration on retention following autoclaving

| Tween Concentration | % retention |
|---|---|
| 0 | 40.0 |
| 25 μg/ml | 8.0 |
| 250 μg/ml | 5.1 |

TABLE 4
Retention in Vials
Comparison of various additives to $^{111}$In-oxine

| | | Retention in vials (%) | |
|---|---|---|---|
| Additive | Concentration | autoclaved | not autoclaved |
| Tween-80 | 200 μg/ml | 6% | 4% |
| Glycerol | 10% | 16% | 8.7% |
| Propylene glycol | 5% | 13% | 7.1% |
| Polyethylene glycol | 5% | 5.5% | 4.5% |
| Ethanol | 5% | 9% | 5% |

TABLE 5
Effect of Tween-80 and Pluronic F-68 on cell labelling efficiency of autoclaved preparations

| | Duplicate Determinations of cell labelling efficiency | |
|---|---|---|
| 0.2M HEPES No additive | 84.8 | 81.6 |
| 0.2M HEPES 250 μg/ml Tween-80 | 82.2 | 83.4 |
| 0.2M HEPES 2.5 mg/ml Pluronic F-68 | 73.9 | 74.4 |

TABLE 6
Effect of Tween-80 concentration on cell labelling efficiency for autoclaved preparations

| Tween-80 | | |
|---|---|---|
| 0 | 69.6 | 69.2 |
| 250 μg/ml | 69.6 | 69.8 |
| 25 μg/ml | 74.3 | 71.0 |

TABLE 7
Comparison of $^{111}$In-oxine in ethanol solution with $^{111}$In-oxine in aqueous solution containing 0.2 M HEPES + 200 μg Tween-80/ml

| | Duplicate determinations of cell labelling efficiency | | | |
|---|---|---|---|---|
| | not autoclaved | | autoclaved | |
| Aqueous preparation with Tween-80 + HEPES 200 μg/ml 0.2 M | 90.3 | 90.3 | 89.4 | 88.5 |
| Ethanolic preparation | 85.3 | 79.3 | | |

TABLE 8
Vial Retention for Preparations of $^{111}$In-oxine with Various Buffers

| Buffer | Autoclaved | Tween-80 | % Vial Retention | | "RCP" |
|---|---|---|---|---|---|
| 25m M HEPES | No | None | 3.6 | 6.2 | Not measured |
| /1 | Yes | None | 18.4 | 16.7 | Not measured |
| None | Yes | 200 ppm | 6.0 | 6.0 | 99% |
| /2 | Yes | None | 30.7 | 35.0 | 88% |
| 25m M TRIS | Yes | 200 ppm | 6.7 | 10.0 | 98% |
| /3 | Yes | None | 22.8 | 17.8 | 99% |
| *25m M MOPS | Yes | 200 ppm | 5.2 | 7.0 | 99% |
| /4 | Yes | None | 24.8 | 13.9 | 98% |

*MOPS = 3-(N-morpholino)propanesulphonic acid
TRIS = Tris-(hydroxymethyl)-methylamine

Clinical Trials

The following formulation was prepared:
Oxine—50 ppm
Tween-80—50 ppm
HEPES—0.025 M
In-111—1 mCi/ml The solution was made isotonic. After dispensing into vials and autoclaving, ten batches had vial retention of radioactivity ranging from 6% to 9% and pH ranging from 6.6 to 6.9.

This formulation proved effective in the labelling of different types of white cell, including leucocytes and platelets. The labelled cells were employed successfully for diagnostic purposes in a large number of patients. Two of the cases are described below.

Case 1

A 55-year old female patient had received a renal transplant 5 days previously. Platelets labelled using the above formulation were used to monitor the organ for possible rejection, and were effective in providing early evidence of rejection and in enabling prompt and successful treatment to be undertaken.

Case 2

A 52-year old male patient who had undergone cholecystectomy developed a post-operative fever. A subphrenic abscess was suspected. Leucocytes labelled using the above formulation were effective in diagnosing an abscess in the upper right quadrant which was later confirmed by surgery.

I claim:

1. An indium-111 composition comprising a complex of indium-111 with a quinoline compound carrying a hydroxyl group in the 8-position, present in an aqueous medium which also contains 10 μg/ml to 1000 μg/ml of a surface active agent.

2. The composition as claimed in claim 1 wherein the quinoline compound is 8-hydroxyquinoline.

3. The composition as claimed in claim 1, wherein the surface active agent is a non-ionic surface active agent.

4. The composition as claimed in claim 1, wherein the surface active agent is selected from polyoxyethylene sorbitan esters of fatty acids.

5. The composition as claimed in claim 1, wherein the concentration of indium-111 is from 0.1 to 10 mCi/ml and the concentration of the quinoline compound is from 5 to 100 μg/mCi of indium-111.

6. The composition as claimed in claim 1, wherein there is also present a non-toxic compatible buffer to maintain the pH in the range 5 to 8.

7. The composition as claimed in claim 6, wherein the buffer is N-2-hydroxy-ethylpiperazine-N'-2-ethanesulphonic acid.

8. The composition as claimed in claim 6, wherein the concentration of the buffer is from 0.02 M to 0.5 M.

* * * * *